United States Patent
Kruzel et al.

(10) Patent No.: US 6,613,741 B2
(45) Date of Patent: Sep. 2, 2003

(54) METHOD FOR TREATING ASEPTIC SIRS IN HUMANS AND OTHER ANIMALS

(75) Inventors: Marian L. Kruzel, Houston, TX (US); Gilbert A. Castro, Houston, TX (US)

(73) Assignee: Ferro Dynamics, Inc., Houston, TX (US)

(*) Notice: Subject to any disclaimer, the term of this patent is extended or adjusted under 35 U.S.C. 154(b) by 55 days.

(21) Appl. No.: 09/430,484

(22) Filed: Oct. 29, 1999

(65) Prior Publication Data

US 2001/0056067 A1 Dec. 27, 2001

(51) Int. Cl.[7] .......................... A61K 38/00; A61K 38/16
(52) U.S. Cl. ............................. 514/12; 514/8
(58) Field of Search ........................ 514/8, 12

(56) References Cited

U.S. PATENT DOCUMENTS

| | | | |
|---|---|---|---|
| 4,977,137 A | | 12/1990 | Nichols et al. ............... 514/6 |
| 5,240,909 A | * | 8/1993 | Nitsche ........................ 514/8 |
| 5,466,669 A | * | 11/1995 | Konig et al. ................. 514/12 |
| 5,531,989 A | * | 7/1996 | Paul ......................... 424/93.4 |
| 5,561,109 A | * | 10/1996 | Mita et al. ................... 514/12 |
| 5,770,580 A | | 6/1998 | Ledley et al. ................ 514/44 |

OTHER PUBLICATIONS

Britigan et al. "The Role of Lactoferrin as an Anti–inflammatory molecule," 1994, Advances in Experimental Medicine and Biology, vol. 357, p. 143–156.*
Medline Abstract, AN 87105804, Fritsch et al., 1987.*
"The Natural History of the Systemic Inflammatory Response Syndrome (SIRS)", M. Sugfrids Raupel–Frauste et al, JAMA, Jan. 11, 1995—vol. 273, No. 2, pp. 117–123.

* cited by examiner

Primary Examiner—Russell Travers
Assistant Examiner—Shengjun Wang
(74) Attorney, Agent, or Firm—Kurt J. Myers

(57) ABSTRACT

The method of the present invention provides a novel use of the iron binding protein lactoferrin to prevent or treat the insult-induced metabolic imbalance in humans and other animals. More particularly, the present invention is the use of lactoferrin for the manufacture of a medicament for the treatment of the metabolic hypo- or hyperactivity in the gut.

12 Claims, 4 Drawing Sheets

METHOD FOR TREATING ASEPTIC SIRS IN HUMANS AND OTHER ANIMALS

RELATED APPLICATIONS

This application is based on PCT application PCT/US98/09053, filed Apr. 30, 1998, entitled "Methods for Preventing and Treating the Insult-Induced Metabolic Imbalance in Humans and Other Animals", which is based on provisional application Serial No. 60/045,521 filed May 3, 1997 entitled "Use of Lactoferrin for Prophylaxis and Therapy of the Systemic Inflammatory Response System in Animals and Humans" which is incorporated herein by reference. This application also relates to U.S. Ser. No. 08/724,586, filed Sep. 30, 1996, entitled "Cloning, Expression and Uses of Human Lactoferrin", which in turn is a continuation of U.S. Ser. No. 08/238,445, filed May 5, 1994, which in turn is a CIP of U.S. Ser. No. 08/132,218, filed Oct. 6, 1993, which in turn is a continuation of U.S. Ser. No. 07/489,186, filed Mar. 8, 1990, all of which are incorporated herein by reference.

FIELD OF THE INVENTION

The present invention relates generally to the iron binding protein lactoferrin. In particular, it relates to the use of lactoferrin to treat or prevent insult-induced metabolic imbalance in humans and animals, and its use for the manufacture of a medicament for the treatment or prevention of insult-induced metabolic imbalance in humans and animals.

BACKGROUND OF THE INVENTION

Homeostasis is a state of equilibrium in the internal environment. The integrity of such system is continuously disturbed by stimuli that tend to create an internal imbalance. In response to prolonged stimuli, the compensatory mechanisms often do not restore the balance. This may, consequently lead to the activation of self-perpetuating, autodestructive mechanisms including death. The central pathway involved in the insult-induced metabolic imbalance may depend in part on the nature of the stimuli, but the hypo- or hyper-thermia appears to be common for many forms of insult. The energy balance of the internal environment is controlled by the central nervous system (CNS) and regulated by the decrease (chills) or increase (fever) of our body temperature. Whether the insult is microbial infection, inflammation or trauma the internal environment responds to those insults by activating thermoregulatory mechanisms that coincide with the production and release of many immunomodulatory substances. Cytokines, prostaglandins, and different growth factors and hormones are released from specific cells to restore the internal metabolic balance, which largely depends on the energy equilibrium.

The significance of lactoferrin in health and disease has been the subject of several reviews. A most recent publication entitled "Lactoferrin: Molecular Structure and Biological Function" has been published in 1995 by B. Lonnerdal and S. Iyer in Ann. Rev. Nutr., 15:93–110.

Lactoferrin is a multifunctional protein expressed in a variety of cell types under different mechanisms of control. The primary function of lactoferrin seems to be a protection against pathogenic bacteria. By virtue of sequestering iron, lactoferrin may control development of potential infections. In addition, it can kill a wide variety of Gram-negative and Gram-positive bacteria by direct interaction with the cell surface, a mode of action that is not dependent on iron.

Lactoferrin is thought to be an important component of the defense system, active at mucosal surfaces, including the gastrointestinal tract. Various immunoregulatory and anti-infective roles for lactoferrin have been reviewed by J. Brock in an article entitled "Lactoferrin: a multifunctional immunoregulatory protein?" and published in Immunology Today (1995), 16:417–419.

Although, considerable data from in vitro experiments indicate several physiological roles for lactoferrin, there is no firm evidence concerning its actual physiological function from in vivo studies. For example, in a review by Roy D. Byens and Werner R. Bezwoda entitled "Lactoferrin and the inflammatory response" and published in the book: Lactoferrin: Structure and Function, pp 133–141, (1994), a relationship between plasma lactoferrin and granulocyte activity in sepsis is mentioned. However, the biological function of the significant amounts of lactoferrin in plasma of septic patients is as yet incompletely understood.

In another review entitled "The role of lactoferrin as an anti-inflammatory molecule" by Bradley E. Britigan, Jonathan S. Serody, and Myron S. Cohen and published in the book: Lactoferrin: Structure and Function, pp 143–156, (1994), the role of lactoferrin in inflammation is suggested to be played at two different levels: (i) as an antioxidant, capable of binding free iron, and (ii) as an endotoxin scavenger, capable of reducing lipopolysaccharide (LPS)-induced toxicity. Furthermore, the ability of lactoferrin to bind LPS in vitro has been confirmed by E. Elass-Rochard, A. Roseanu, D. Legrand, M. Trif, V. Salmon, C. Motas, J. Montreuil and G. Spik in an article entitled "Lactoferrin-lipopolysaccharide interaction: involvement of the 28–34 loop region of human lactoferrin in the high-affinity binding to Escheria coli O55B5 lipopolysaccharide", published in Biochem. J. (1995) 312:839–845. However, in vivo studies have to confirm lactoferrin's role in those internal metabolic responses during inflammatory processes.

In another article entitled: "Lactoferrin can protect mice against a lethal dose of Escherichia coli in experimental infection in vivo" by T. Zagulski, P. Lipinski, A. Zagulska, S. Broniek and Z. Jarzabek, published in 1989 in Br. J. Exp. Path., 79:697–704, the use of lactoferrin is disclosed to increase the survival of mice injected with a lethal dose of bacteria. However there is no disclosure that the intravenously administered lactoferrin has any effect on the gut function and structure to give such protection.

Relevant patents are also silent as to the role of lactoferrin in insult-induced metabolic activity.

U.S. Pat. No. 4,977,137 of Nichols et al. discloses milk lactoferrin as a dietary ingredient which promotes growth of the gastrointestinal tract of human infants and newborn nonhuman animals immediately on birth. Nichols discusses the use of lactoferrin in the management of short gut syndrome, an anatomical dysfunction rather than an insult-induced metabolic imbalance.

U.S. Pat. No. 5,240,909 of Nitsche relates to the use of lactoferrin as an agent for the prophylactic and therapeutic treatment of the toxic effects of endotoxins. Nitche discloses that the lactoferrin used according to his invention has the ability to neutralize endotoxin and must have bound to it either iron or another metal to be effective.

U.S. Pat. No. 5,066,491 of Stott et al. encompasses a method of disease treatment utilizing a therapeutically effective product produced from ordinary milk whey.

SUMMARY OF THE INVENTION

The method of the present invention provides a novel use of the iron binding protein lactoferrin to prevent or treat insult-induced metabolic imbalance in humans and other animals. In one embodiment of the present invention there is provided a method to use lactoferrin to modulate such metabolic imbalance through the gastrointestinal tract. In a further embodiment, the present invention relates to the use of lactoferrin for the manufacture of a medicament for the prevention or treatment of insult-induced metabolic imbalance in humans and animals. In yet a further embodiment, the present invention relates to the use of lactoferrin for the manufacture of a medicament for the modulation of such metabolic imbalance through the gastrointestinal tract.

Figure 1:
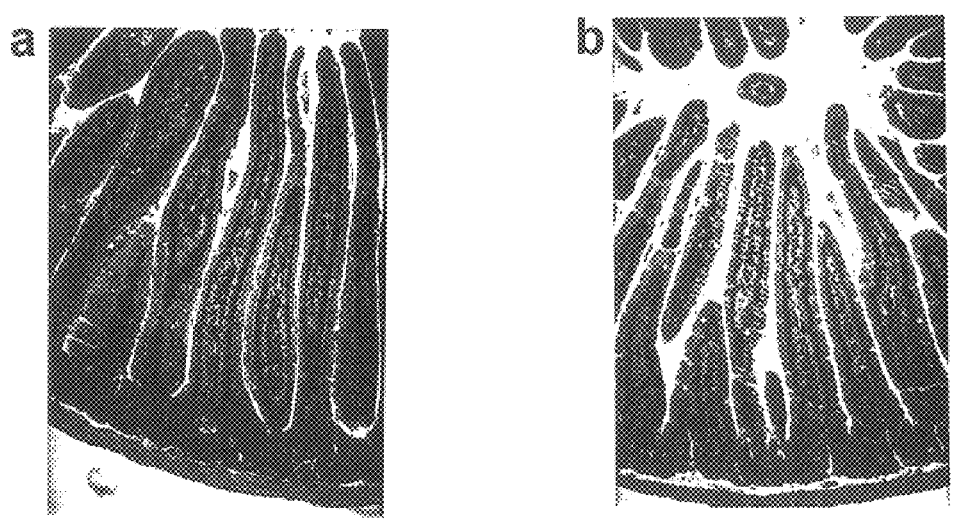
FIG. 1 Illustrates histological sections of mouse jejunum stained with hematoxylin and eosin to visualize intestinal structures during 21 days treatment with lactoferrin (a) or saline (b).

Table 1. Illustrates jejunal responses to glucose and chloride secretagogues after long term treatment with lactoferrin.

Table 2. Illustrates jejunal responses to glucose and chloride secretagogues following infection with *Trichinella spiralis*

DESCRIPTION OF THE PREFERRED EMBODIMENTS

The maintenance of homeostasis is essential for cellular integrity and the wellness of our body. Inflammation is one of those compensatory mechanisms in response to external insult. When excessive in magnitude or duration, however, the otherwise beneficial effects of inflammation may be deleterious, impacting negatively on the recovery or healing of the host. As illustrated below, acute inflammation caused by an external insult may be repaired or it may develop into a slow progressing chronic condition such as inflammatory bowel disease (IBD), rheumatoid arthritis (RA) or into fast progressing systemic inflammatory response syndrome (SIRS), as defined in Table 1, page 119, of "The Natural History of the Systemic Inflammatory Response Syndrome (SIRS)", M. Sigfrido Rangel-Frausto et al., JAMA, Jan. 11, 1995—Vol 273, No. 2, pp 117–123, incorporated herein by reference in its entirety, including sepsis, septic shock, and multiple organ failure (MOF):

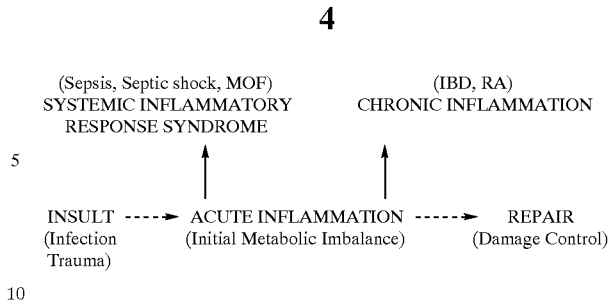

When tissue damage occurs, particularly if it is induced by infection during trauma, the vascular effects of the repair mechanisms are immediate. The tissue becomes inflamed at the site of injury, with the tissue spaces and the lymphatics blocked by fibrin clots. The fluid barely flows through the inflamed tissue, therefore the spread of bacteria and/or their toxic products is delayed. Unlike the immune responses, which may take days to develop, the vascular effects of inflammation occur in seconds and coincide with the burst of inflammatory cytokines, such as tumor necrosis factor (TNFα) and interleukin-1 (IL-1β), from activated monocytes/macrophages. Subsequent to the release of cytokines is an acute increase in neutrophils in the blood. Large numbers of neutrophils begin to invade the tissues that attract these cells. Although generally beneficial to the host, inflammatory processes are intrinsically destructive to the surrounding tissues and potentially can result in major tissue injury. Furthermore, the inflammatory response can spread from the local environment and induce generalized systemic response which may become self-perpetuating by overproduction of pro-inflammatory cytokines.

According to the present invention, the feedback control mechanism of inflammation depends on the presence of lactoferrin. By blocking the deleterious effects of the pro-inflammatory cytokines, lactoferrin provides a feedback mechanism for the metabolic imbalance during development of systemic inflammation, and thus, can be used in accordance with the present invention in a method for treating or preventing such insult-induced metabolic imbalance.

The gastrointestinal tract may be viewed as an ecological system that acts to maintain balance between the host and the bacterial flora. Two major host components appear to be involved in maintaining this balance. The first is a non-specific structural barrier provided by the epithelial layer of the gastrointestinal mucosae. The second component involves functional immunological elements found in the mucosal and submucosal compartments, e.g., gut associated lymphoid tissue. When the gut integrity is disrupted by invasive pathogens or by trauma, a myriad of pro-inflammatory mediators is released from cells in the gut wall that exert actions in the tissue or gut lumen. The gut responses to such insults are immediate to protect the internal environment from enteric bacteria crossing the gut barrier and inducing systemic responses. Therefore, it is of great importance to preserve the structure and function of the gastrointestinal tract during initial stages of such metabolic imbalance to avoid the systemic translocation of the enteric bacteria.

According to the present invention the gastrointestinal tract is considered the key organ to provide compensatory mechanisms to any type of insult-induced metabolic imbalance. The present invention, by in vivo experiments on gut, shows that lactoferrin attenuates the severity of the insult-induced metabolic imbalance, thereby protecting the development of severe hypo- or hyperactivity that often leads to chronic inflammation or systemic inflammatory response syndrome. Furthermore, it has been found that lactoferrin can be used in accordance with the present invention in a method for protecting intestinal functions during insult-induced metabolic imbalance. The evidence presented herein confirms that lactoferrin administered either enterally or parenterally helps to maintain physiological balance in normal and pathologic gut situation.

Insult is defined herein as any intervention in the internal environment including microbial, viral or parasitic infections; stress; trauma; insufficient or excessive nutrient intake; invasive or non-invasive medical procedures, any of which cause metabolic imbalance, a state of disturbed integrity of the internal system. Usually, such metabolic imbalance is referred to as hypo- or hyper-activity of the internal system.

The present invention is to use lactoferrin administered to the gut for treating or preventing metabolic imbalance during insult-induced hypo- or hyper-activity often manifested by inflammation as a result of such insult.

Lactoferrin is one of the most abundant proteins found at mucosal surfaces and within secondary granules of neutrophiles in all vertebrates. The highest concentration of lactoferrin has been found in mammary glands of lactating females. The sequence homology between human and other species lactoferrins is between 50% to 70%. Bovine milk lactoferrin, which is commercially available, is about 69% identical to its human counterpart. Due to this fact, the clinical application of bovine lactoferrin in humans is limited to oral administration; any type of systemic administration of bovine lactoferrin in humans would cause highly antigenic reaction.

Lactoferrin for use in a present invention may be human lactoferrin from human breast milk or extracted from milk of other animals such as bovine lactoferrin from cow's whey. Due to severe limitations on availability of large quantities of human breast milk and the FDA requirements, it may be difficult to develop a commercial production of clinically acceptable natural human lactoferrin. Consequently, recombinant DNA technology is considered the best solution to obtaining large quantities of reliable human or bovine lactoferrins which would be consistent in production, uniform in its biological properties, and non-pathogenic.

The preferred lactoferrin is lactoferrin expressed in a yeast expression system such as *Pichia pastoris* or *Hansenula polymorpha*, or in an eukaryotic expression system. The preferred lactoferrin is described in U.S. Ser. No. 08/724,586, filed Sep. 30, 1996, entitled "Cloning, Expression and Uses of Human Lactoferrin" and PCT/US95/05653, filed May 5, 1995. Other recombinant lactoferrins are described in U.S. Pat. Nos. 5,571,691; 5,571,697; and 5,571,896, all of which are incorporated herein by reference.

Lactoferrin is administered in accordance with the present invention either enterally, preferably orally, in the form of a powder, solution or gel, or parenterally, preferably intravenously, in the form of an injectable solution, as an aid to treat or prevent metabolic imbalance. Preferable formulations or medicaments of the present invention comprise lactoferrin alone or in combination with carriers such as, saline, silica, talcum, stearic acid, its magnesium or calcium salt, polyethyleneglycol, and fatty emulsions and suspensions that will be readily apparent to the skilled artisan. The lactoferrin is preferably present in the formulation at a level of 0.01 milligram to 2 milligram, more preferably between 0.1 to 1 milligram, based on 1 milliliter or 1 gram of the carrier. An effective amount of lactoferrin varies depending on the individual treated, severity of the insult-induced metabolic imbalance and the form of administration. Preferable in treating mammals, a single or twice daily dose of 0.01 milligram to 20 milligrams, more preferable 0.1 milligram to 1 milligram of lactoferrin per kilogram of body weight or per 1.0 square inch of targeted area is administrated.

The effectiveness of lactoferrin in the treatment or prevention of insult-induced metabolic imbalance according to the present invention is demonstrated below in different types of insults in a mouse model: (i) parasitic infection with *Trichinella spiralis*, and (ii) LPS endotoxemia. Injection with LPS, a derivative of the cell wall of Gram negative bacteria, is commonly used as the insult for study of sepsis or MOF. The insults were chosen either at excessive levels to exemplify the effect of lactoferrin under acute conditions such as sepsis or multiple organ failure or at lower levels to illustrate the effect of lactoferrin on stress or trauma in mice. Also, the route of administration of lactoferrin or saline by gavage, intravenously or intraperitoneally exemplify the effects of noninvasive or invasive medical procedures on the internal environment. The following objectives were evaluated: (i) safety of a long term oral administration of lactoferrin, (ii) effects of lactoferrin on the gut caused by intestinal infection with *Trichinella spiralis*, and (iii) the effects of lactoferrin on the metabolic activity during LPS-induced endotoxemia, all in a mouse model.

The procedures and methods for determining the physiological function of the gut under different type of insults are summarized as follows. These procedures have been developed to measure the state of the gut as normal, returned to normality, or pathologic using saline-treated animals as a control. Human lactoferrin has been used replaceable with its bovine counterpart. Only male CF-1 mice (Harlan, Houston, Tex.), are used throughout this investigation. Mice are housed in groups of three per cage and are given stock diet (F6 Rodent Diet 8664, Teklad, Madison, Wis.) and water at libitum. Daily food consumption and body weight are measured each morning. Both food intake and body weight is expressed as the average for each group. The electrophysiological parameters are measured on jejunal segments obtained from mice under anesthesia. Briefly, jejunum, beginning 1 cm distal to the ligament of Treitz, is removed, rinsed in Krebs-Ringer bicarbonate (KRB) solution, pH 7.4, and slit open along the mesenteric border. Consecutive one-cm full thickness segments are taken from the proximal part of the intestine and mounted as a flat sheet between two Ussing half chambers with an aperture of 0.512 $cm^2$. Tissues, bathed on their mucosal and serosal sides with 10 ml KRB solution, are voltage clamped at zero transepithelial potential using a VCC-600 voltage current clamp (Physiologic Instruments, San-Diego, Calif.). A continuous record of short circuit current with respect to time is obtained and recorded on a BD-41 Kipp & Zonen recorder (Delft, Holland). To measure tissue resistance, a current that generates an extra 1 mV potential difference across the tissue from a pulse generator in the voltage clamp apparatus is passed every two min for 0.1 sec. Resistance is calculated using Ohm's law (V=IR). Changes in short circuit current ($\Delta$Isc) induced by $Cl^-$ secretagogues [serotonin (5-HT) and carbamylcholine (CCh)] and by glucose are presented as the maximal elevation and are expressed as $\Delta A/cm^2$. To perform histological evaluation the jejunal segments are fixed in 10% formalin and embedded in paraffin using standard techniques. Section 5 $\mu$m thick are cut and stained with hematoxylin and eosin and with periodic acid/Schiff (PAS) to visualize brush border and epithelial mucin. Sections are examined by light microscopy and photographs are taken with a Nikon Optiphot microscope. Student t-test and two way ANOVA (Snedecor 1980) are used to compare means among the different groups. The results are expressed as means ±SE. P value of 0.05 or less was considered significant.

The following examples are presented herein to illustrate the present invention:

I. Long Term Administration of Lactoferrin Using Gavage as a Non-invasive Route of Administration

EXAMPLE 1

Naive mice were gavaged daily with human lactoferrin (1 mg/100 µl saline) for 21 days each morning. Their control counterparts were given 100 µl of saline for the same time period. After 21 days of treatment all mice were killed and jejunal segments were obtained for electrophysiological measurements and histological examination.

Food consumption and cumulative weight gain in mice fed lactoferrin were similar in both lactoferrin and saline-treated mice. Basal electrophysiological parameters of mouse jejunum [intestinal transepithelial resistance (R), potential difference (PD) and short circuit current (SCC)] were not altered by long term administration of lactoferrin. Likewise, intestinal glucose absorption, and $Cl^-$ secretion induced by 5-HT (serotonin), CCh, or histamine were not affected by three weeks administration of lactoferrin (Table 1). Also, the histology of the intestine was not altered in mice fed lactoferrin (FIG. 1).

The results show that there are no adverse effects of enteral administration of lactoferrin on gut structure and function.

II. The Effects of Lactoferrin on the Intestinal Metabolic Activity Induced by Infection with *Trichinella spiralis*

EXAMPLE 2

Human lactoferrin (1 mg/100 µl saline) was given to mice orally by gavage for three consecutive days. Their counterparts were given 100 µl of saline. On day four, one half of all animals from each group were infected with 600 *Trichinella spiralis* larvae. For seven additional days mice receive either lactoferrin or saline. At this time all mice were killed and jejunal segments were removed for electrophysiological and histological studies.

Figure 2:
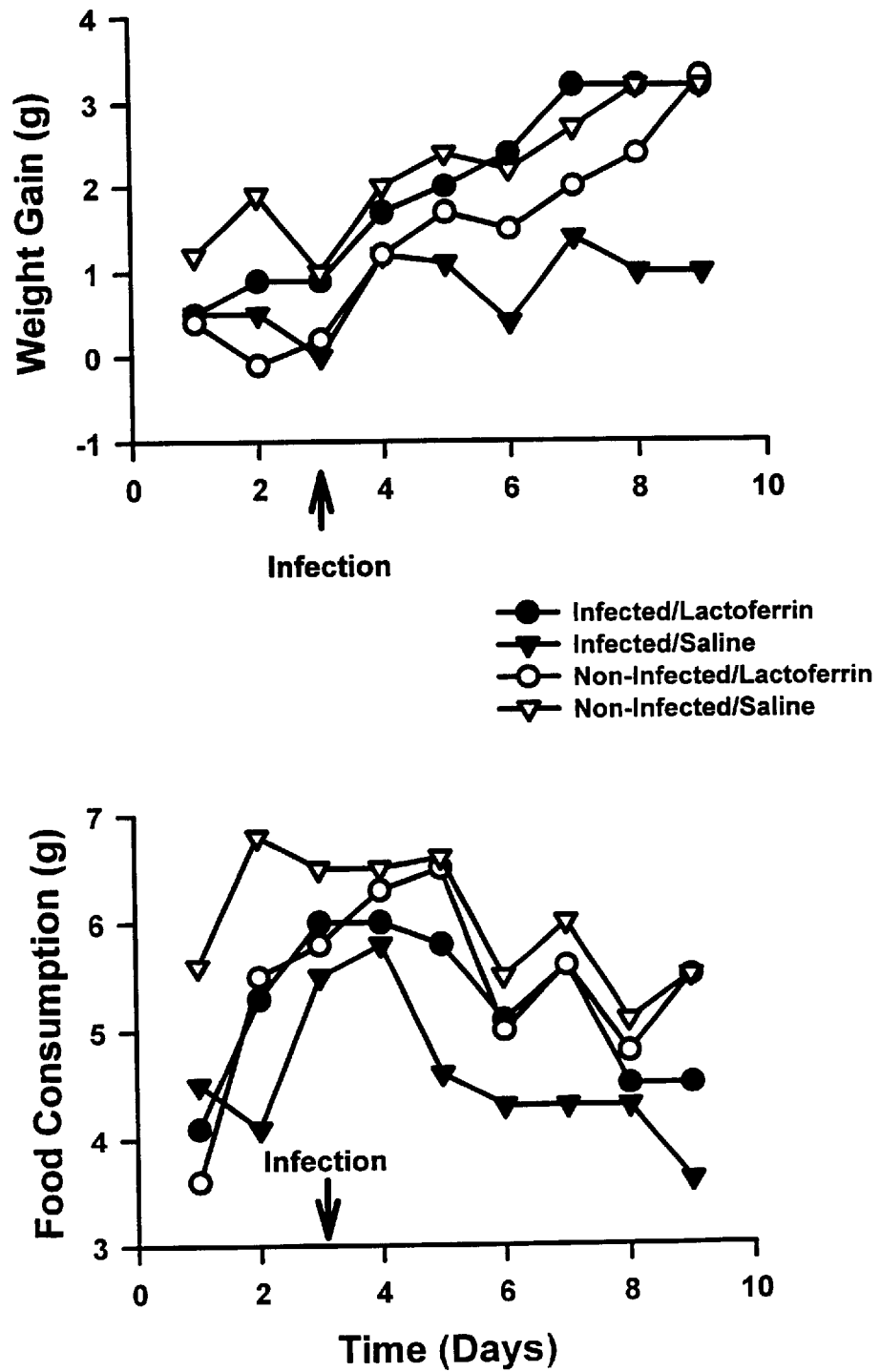
FIG. 2 Illustrates the cumulative weight gain and daily food consumption in mice that have been treated with either lactoferrin or saline during experimental infection with *Trichinella spiralis*.

When lactoferrin was given to mice for three days prior to infection with *Trichinella spiralis* and seven days thereafter, the reduction in food consumption, normally caused by the infection, was not as marked (FIG. 2). The same effect was evident in the cumulative weight gain. Mice treated with lactoferrin gained weight following infection at the same rate as noninfected mice, while infected animals given saline lagged in their weight gain when compare to all other groups.

Resistance of the intestinal tissue seven days after infection was comparable among infected and noninfected groups. The group of mice fed lactoferrin and infected with the parasite showed an increase in SCC, when compared with all other groups, however the difference was not statistically significant. Jejunal PD in the infected mice fed with lactoferrin also was higher, although not significant, when compared to that of infected mice given saline. Intestinal glucose absorption was significantly reduced in infected groups, regardless of treatment (Table 2). Although infection reduced secretion, jejunum from mice that received lactoferrin before and after inoculation with *Trichinella spiralis* showed a greater capacity to secrete $Cl^-$ in response to CCh (but not to 5-HT) than did mice given saline (Table 2).

Figure 3:
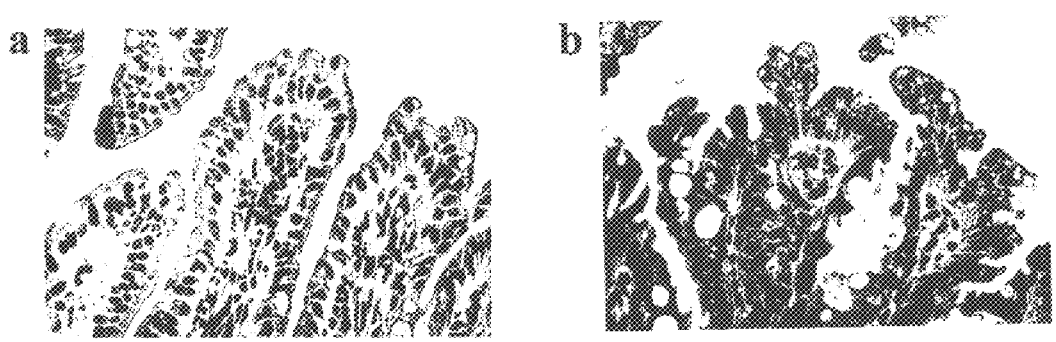
FIG. 3 Illustrates histological sections of mouse jejunum stained with hematoxylin and eosin to visualize intestinal structures during experimental infection with *Trichinelia spiralis* a) infected, lactoferrin-treated, b) infected, saline-treated.

At day seven post-infection with *Trichinella spiralis*, the inflammatory process in the intestinal mucosa was at its peak. Histological sections of jejunum stained with hematoxylin and eosin showed that lactoferrin had a protective effect on the intestinal epithelium (FIG. 3). Infection with *Trichinella spiralis* caused a diffused enteritis in control mice with swelling of the villi and enlargement of the crypts. The intestinal epithelium exhibited severe vacuolar degeneration, papiliarization, pseudostratification and shedding of epithelial cells. In the lactoferrin treated mice vacuolar degeneration was confined to scattered, single cells, while papiliarization and pseudostratification were absent. Inflammatory cell infiltration of the mucosa appeared similar in the lactoferrin-treated mice and in their control counterparts. However, intestinal stromal swelling was reduced in the lactoferrin-treated mice. Also, the number of mitotic cells was 2–3 times higher in lactoferrin treated animals than that of saline controls. Staining intestinal sections for carbohydrates demonstrated that lactoferrin significantly enhanced the production of mucin, a common marker of goblet cells. The following average counts of goblet cells per villi were obtained from the histological section by light microscopy: a) saline-treated, noninfected mice 7.1 (n=2), b) lactoferrin-treated, noninfected mice 10.9 (n=3), c) saline-treated, infected mice 10.2 (n=2), d) lactoferrin-treated, infected mice 16.2 (n=3). The increase in the intestinal goblet cell number in lactoferrin-treated, non-infected mice was 53% when compared with their saline-treated, noninfected counterparts. A similar increase (58%) was observed in lactoferrin-treated, infected mice when compared with their saline-treated, infected counterparts.

It is evident that the intestinal damage due to parasitic infection is significantly reduced in lactoferrin-treated animals. These important observations suggest that lactoferrin protects intestinal function during insult-induced metabolic imbalance.

EXAMPLE 3

This experiment was designed to test the effect of lactoferrin on the establishment of *Trichinella spiralis* larvae in mouse intestine, after inoculation with infective worms. Mice were given human lactoferrin (1 mg/100 µl saline) orally by gavaging for three consecutive days. The control group was given saline. On day four, following three days of treatment, mice were infected with 600 *Trichinella spiralis* larvae. Twenty four hours later worms were collected from the gut and counted.

The number of *Trichinella spiralis* infective larvae that established in the intestine of mice fed lactoferrin supplemented diet for three days prior to infection was lower than in their counterparts (152±10.8; n=6 versus 211.8±25.6; n=6). It is evident that lactoferrin attenuates the establishment of infective larvae in mouse intestine.

II. The Effects of Lactoferrin on the Metabolic Activity in Endotoxemic Mice

The administration of lactoferrin was performed in a non-invasive procedure such as gavage or in an invasive procedure such as intravenously or intraperitoneally.

EXAMPLE 4

The effect of human lactoferrin on the development of LPS-induced endotoxemia in mice was determined by examining survival of mice upon challenge with a lethal dose of LPS. Naive mice were injected once intraperitoneally with 150 μl of saline solution lactoferrin (7.5 mg/mouse) one hour before or after LPS challenge. This illustrates both a prophylactic and therapeutic treatment. Their control counterparts were given 150 μl of saline. Bacterial LPS (*E. coli*, Serotype 0111:B4) was given intraperitoneally at the lethal dose of $1.5 \times 10^6$ endotoxic units per mouse. The survival of mice was monitored over the period of time of four weeks (n=6 per each group).

| Treatment | Survival (%) |
|---|---|
| LPS | 16.6 |
| Lactoferin followed by LPS (prophylactic application) | 83.3 |
| LPS found by Lactoferrin (therapeutic application) | 66.6 |

A single intraperitoneal dose of lactoferrin (7.5 mg) administered 1 hour before or after LPS challenge significantly increased the survival of mice.

EXAMPLE 5

The effectiveness of oral administration of lactoferrin on survival of mice subjected to lethal injection of LPS was determined in the following experiment. Naive mice were gavaged with 150 μl of saline solution of bovine lactoferrin (7.5 mg/dose) for three days prior or after LPS challenge. Their control counterparts were given 150 μl of saline. Bacterial LPS (*E. coli*, Serotype 0111:B4) was given intravenously at the lethal dose of $1.5 \times 10^6$ endotoxic units per mouse. The survival of mice was monitored over the period of time of four weeks (n=6 per each group).

| Treatment | Survival (%) |
|---|---|
| LPS | 37.5 |
| Lactoferin followed by LPS (prophylactic application) | 50 |
| LPS followed by Lactoferrin (therapeutic application) | 83.3 |

Oral administration of lactoferrin for three days prior or after intravenous administration of LPS increased significantly the survival of mice.

EXAMPLE 6

Also, the protective effect of lactoferrin on survival of mice subjected to lethal injection of LPS was determined by administering lactoferrin intravenously. Naive mice were injected intravenously with 150 μl of saline solution of bovine lactoferrin (7.5 mg/dose) for three days prior or after LPS challenge. Their control counterparts were given 150 μl of saline. Bacterial LPS (*E. coli*, Serotype 0111:B4) was given intravenously at the lethal dose of $1,5 \times 10^6$ endotoxic units per mouse. The survival of mice was monitored over the period of time of four weeks (n=6 per each group).

| Treatment | Survival (%) |
|---|---|
| LPS | 37.5 |
| Lactoferrin followed by LPS (prophylactic application) | 100 |
| LPS followed by Lactoferrin (therapeutic application) | 100 |

Intravenous administration of lactoferrin for three days prior or after intravenous administration of LPS provides total protection from a lethal dose of LPS.

EXAMPLE 7

The effect of lactoferrin on electrophysiological parameters of gut function in mice challenged with a lethal dose of LPS was determined in the following experiment. Naive mice (n=6 per each group) were injected intraperitoneally with a lethal dose of LPS ($1.5 \times 10^5$ endotoxic units per mouse). One hundred microliters (100 μl) of saline solution of human lactoferrin (10 mg/ml) was given to mice enterally by gavaging at 1 hour, 3 hours and 6 hours post-LPS challenge. Their counterparts were given saline. Twenty four hours later the blood samples were collected, mice were sacrificed and jejunal segments removed for electrophysiological and histological measurements.

Treatment of mice with lactoferrin had no effect on the electrophysiological characteristics of jejunal epithelium. Resistance (R) of the intestinal tissue following LPS challenge was significantly lower in both lactoferrin treated mice and saline control. Mice fed lactoferrin and challenged with LPS showed a moderate increase in short circuit current when compared with saline control. PD was comparable for all groups. Glucose absorption was about 30% higher for LPS-challenged animals with no significant difference between lactoferrin treated and saline control. Cl— secretory response to 5-HT and CCh was also elevated in both LPS groups.

Figure 4:
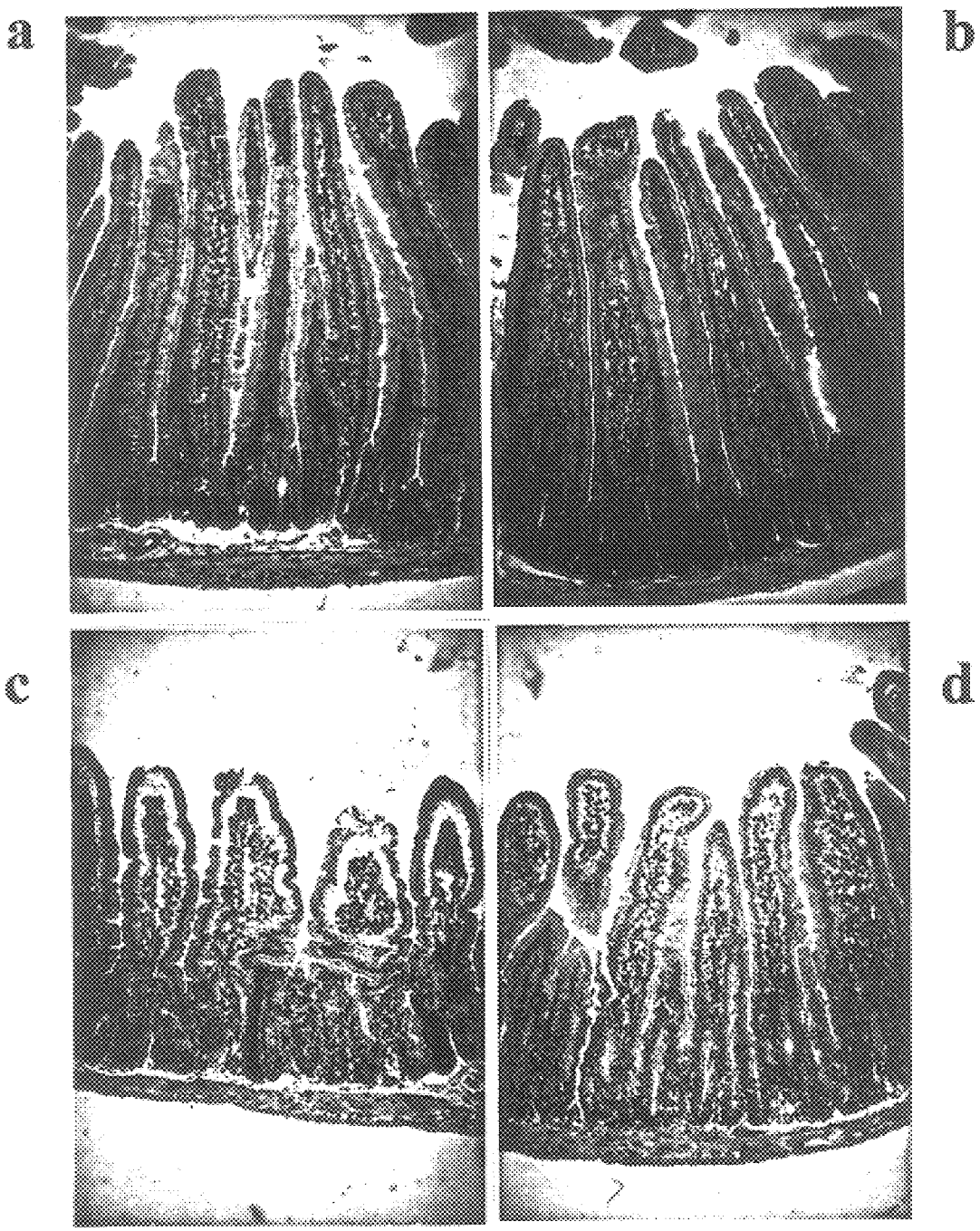
FIG. 4 Illustrates histological sections of mouse jejunum stained with hematoxylin and eosin to visualize intestinal structures during experimental endotoxemia a) non-infected, saline control, b) non-infected, lactoferrin-treated, c) infected, saline-treated, d) infected, lactoferrin-treated.

The intestinal epithelium of mice injected with LPS exhibited severe vacuolar degeneration in control animals with shortening and shrinking of the villi and expansion of the crypts. There were heavy inflammatory infiltrates in the tunica mesenteris of control animals (FIG. 4). In the lactoferrin-treated mice vacuolar degeneration was less pronounced with the epithelium resembling the highly polarized, resorbtive epithelium of non-infected mice.

This protective effect of lactoferrin on gut function and structure during experimental endotoxemia correlates with significant reduction of cytokines in plasma. It has been shown that lactoferrin attenuates the release of TNFα and IL-1β into plasma by more than 50% when measured 2 hours post LPS challenge. However, only an insignificant decrease in the concentration of those cytokines was observed in the intestinal tissue homogenates.

It is evident, that lactoferrin helps to maintain the physiological function of the gut during LPS-induced metabolic imbalance.

EXAMPLE 8

The thermoregulatory effects of lactoferrin were tested on endotoxemic mice by measuring body temperature in conjunction with production of pro-inflammatory cytokines. Naive mice were injected intravenously with 150 μl of saline solution of bovine lactoferrin (7.5 mg/mouse). Their control counterparts were given 150 μl of saline. One hour later all mice were challenged intravenously with LPS at the dose of $3.75 \times 10^5$ endotoxic units per mouse. Two hours later mice were anesthetized, temperature was measured and blood was collected. The concentration of pro-inflammatory cytokines in plasma and tissue homogenates was measured by Enzyme-linked immunoabsorbent assay (ELISA) using specific antibodies for each antigen.

| Treatment | TNFα pg/ml | IL-1β pg/ml | IL-6 pg/ml | Temperature ° C. |
|---|---|---|---|---|
| Saline | 0.00 ± 0.00 | 11.52 ± 1.40 | 9.3 ± 3.6 | 38.16 ± 0.21 |
| Lactoferrin | 1.60 ± 1.60 | 1.45 ± 0.93 | 12.1 ± 2.2 | 36.33 ± 0.24 |
| LPS | 694.4 ± 125.9 | 128.3 ± 14.2 | 23,566 ± 2,466 | 35.16 ± 0.21 |
| Lactoferr./LPS | 280.5 ± 36.8 | 26.1 ± 4.43 | 7,144 ± 1,403 | 36.91 ± 0.08 |

Statistically significant differences were found between lactoferrin-treated mice and their control counterparts for all parameters measured (n=6 per each group). Lactoferrin attenuates the release of TNFα, IL-1β, and IL-6 into plasma and modulates the decrease of body temperature that is due to the insult-induced metabolic imbalance. Moreover, the effect of lactoferrin on the thermogenesis is confirmed by the fact that lactoferrin interplays with the major thermoregulatory factor nitric oxide during insult-induced hypo- or hyper-activity.

It is evident from all the foregoing examples that lactoferrin given either orally or systemically is capable of modulating the gut function during insult-induced metabolic imbalance by protecting intestinal epithelium. We have demonstrated that such protection of gut function have inhibitory systemic effect on development of autodestructive mechanisms including death. Both prophylactic and therapeutic applications of lactoferrin have been shown to be effective in accordance with the present invention.

TABLE 1

| | Treatment | |
|---|---|---|
| Parameter | Lactoferrin n = 6 | Saline n = 6 |
| | $\Delta I_{sc}$ ($\mu A/cm^2$)[b] | |
| Glucose ($10^{-2}$ M)[c] Chloride Secretion | 136.6 ± 19.6 | 163.2 ± 7.6 |
| 5-HT ($10^{-4}$ M)[d] | 93.1 ± 13.4 | 71.2 ± 10.8 |
| CCh ($10^{-4}$ M)[d] | 146.8 ± 18.8 | 121.5 ± 10.1 |
| Histamine ($10^{-4}$ M)[d] | 78.7 ± 14.9 | 49.6 ± 3.6 |

[a]Lactoferrin (1 mg/day/mouse) was administered by gavage for twenty one days prior to making measurements.
[b]Values are means ± S.E.
[c]Added to mucosal side.
[d]Added to serosal side.

What is claimed is:

1. A method which comprises administering to a patient having aseptic systemic inflammatory response syndrome (SIRS) a therapeutically effective amount of lactoferrin for blocking the deleterious effects of pro-inflammatory cytokines.

2. The method of claim 1 wherein said lactoferrin is bovine milk lactoferrin.

3. The method of claim 1 wherein said lactoferrin is human recombinant lactoferrin.

4. The method of claim 1 wherein said lactoferrin is administered as a pharmaceutical or nutritional composition in admixture with an acceptable carrier.

5. A method which comprises administering to a patient having aseptic systemic inflammatory response syndrome (SIRS) a therapeutically effective amount of lactoferrin for reducing hyper- or hypothermia.

6. The method of claim 5 wherein said lactoferrin is bovine milk lactoferrin.

7. The method of claim 5 wherein said lactoferrin is human recombinant lactoferrin.

8. The method of claim 5 wherein said lactoferrin is administered as a pharmaceutical or nutritional composition in admixture with an acceptable carrier.

9. A method for the prophylactic treatment of the progression of systemic inflammatory response syndrome (SIRS) into sepsis, severe sepsis, septic shock and multiple organ failure comprising administering to a patient having aseptic SIRS an effective amount of lactoferrin.

TABLE 2

| | Glucose ($10^{-2}$ M)[b] | | 5-HT ($10^{-4}$ M)[b] | | CCh ($10^{-4}$ M)[b] | |
|---|---|---|---|---|---|---|
| Treatment | Non-infected | Infected | Non-Infected | Infected | Non-infected | Infected |
| | $\Delta I_{sc}$ ($\mu A/cm^2$) | | | | | |
| Lactoferrin[c] | 130.0 ± 25.1 (6)[I] | 43.0 ± 18.5 (6)[II] | 74.0 ± 13.0 (6)[I] | 46.0 ± 15.0 (6)[II] | 98.0 ± 3.1 (6)[I] | 72.0 ± 24.0 (6)[I] |
| Saline | 128.0 ± 19.4 (6)[I] | 30.0 ± 16.5 (6)[II] | 71.0 ± 10.0 (6)[I] | 28.0 ± 10.0 (6)[II] | 121.0 ± 15.0 (6)[I] | 24.0 ± 10.0 (6)[II] |

[a]Mice were inoculated with 600 *T. spiralis* larvae. Measurements were taken seven days later.
[b]Values are mean ± S.E. (n).
[c]Lactoferrin (1 mg/day/mouse) was administered by gavage for three consecutive days prior to infection with *T. spiralis* and for seven days thereafter.
[I, II]Different Roman numerals indicate significant statistical difference between values when comparing all four experimental groups using two way ANOVA followed by Duncan multiple comparison test.

10. The method of claim 9 wherein said lactoferrin is bovine milk lactoferrin.

11. The method of claim 9 wherein said lactoferrin is human recombinant lactoferrin.

12. The method of claim 9 wherein said lactoferrin is administered as a pharmaceutical or nutritional composition in admixture with an acceptable carrier.

* * * * *